United States Patent [19]

Barnett

[11] Patent Number: 4,981,147
[45] Date of Patent: Jan. 1, 1991

[54] COITAL PROTECTIVE GARMENT

[76] Inventor: Madeleine C. Barnett, 2302 Malraux Dr., Vienna, Va. 22280

[21] Appl. No.: 243,178

[22] Filed: Sep. 8, 1988

Related U.S. Application Data

[63] Continuation of Ser. No. 74,888, Jul. 17, 1987, abandoned.

[51] Int. Cl.⁵ .......................... A61F 6/02; A61F 6/06
[52] U.S. Cl. ..................... 128/842; 128/844; 128/830
[58] Field of Search ................. 128/842–845, 128/DIG. 26, 830; 604/349, 352, 353; 2/400, 401, 402, 403, 404

[56] References Cited

U.S. PATENT DOCUMENTS

| 87,932 | 3/1869 | Hoffman | 604/349 |
|---|---|---|---|
| 1,123,994 | 1/1915 | Cranston | 128/128 |
| 1,680,178 | 8/1928 | Shafer | 2/402 |
| 1,721,343 | 7/1929 | Hoover | 2/402 |
| 1,723,833 | 8/1929 | Young | 2/402 |
| 1,986,988 | 1/1935 | Treadnell | 128/136 |
| 2,591,783 | 4/1952 | Craddock | 604/353 |
| 3,043,307 | 7/1962 | Weston | 604/349 |
| 3,207,155 | 9/1965 | Casey | 2/403 |
| 3,353,538 | 11/1967 | Carrigan | 604/352 |
| 3,536,066 | 10/1970 | Ludwig | 128/132 R |
| 3,554,195 | 1/1971 | Murdoch | 2/402 |
| 3,648,700 | 3/1972 | Warner | 604/349 |
| 3,677,225 | 7/1972 | Czirely | 604/352 |
| 3,721,243 | 3/1973 | Hesterman et al. | 604/353 |
| 4,014,044 | 3/1977 | Figeroa et al. | 128/138 R |
| 4,068,315 | 1/1978 | Rainville | 2/404 |
| 4,280,230 | 7/1981 | LaFleur | 2/406 |
| 4,378,010 | 3/1983 | McDonald | 128/DIG. 26 |
| 4,446,860 | 5/1984 | Gutnick | 128/132 R |
| 4,553,968 | 11/1985 | Komis | 604/353 |
| 4,568,340 | 2/1986 | Giacalone | 604/353 |
| 4,599,751 | 7/1986 | Bouwhuis | 128/138 R |
| 4,664,104 | 5/1987 | Jaicks | 604/353 |
| 4,698,855 | 10/1987 | Hicks | 2/403 |

FOREIGN PATENT DOCUMENTS 1158507 12/1983 Switzerland .................. 604/349

OTHER PUBLICATIONS

"Lavetra ® Rundum-Sicher-Condom", undated product literature of Lavetra GmbH (West Germany) for Lavetra Universal Safety Condom.
*The Internist,* "The Many Costs of AIDS", vol. XXVIII, No. 4, pp. 3, 5–28, 30, 42, 50–56, Apr. 1987 (American Society of Internal Medicine).

*Primary Examiner*—Robert A. Hafer
*Assistant Examiner*—Kevin G. Rooney
*Attorney, Agent, or Firm*—Steven J. Hultquist

[57] ABSTRACT

A unitary coital protective garment, comprising a groin covering panel formed of a flexible, resilient, liquid-impenterable material, and a penile sheath integrally formed with the groin covering panel, having a closed distal end, and formed of flexible, resilient, liquid-impenetrable material, integrally leak-tightly joined at its proximal end to the groin covering panel to enable penis insertion into the penile sheath, with the panel being circumferentially continuous around the proximal end of the sheath at its integral junction with the panel. Wrap-around, athletic supporter, apron, and panty-types of construction of the garment may be variously employed. The garment of the invention provides enhanced protection to the wearer and coital partner, and may be advantageous in reducing the risk of transmission of venereal and/or immunosuppressive diseases.

6 Claims, 2 Drawing Sheets

COITAL PROTECTIVE GARMENT

This application is a continuation of Ser. No. 07/074,888, filed July 17, 1987, now abandoned.

BACKGROUND OF THE INVENTION

1. Field of the Invention

The present invention relates generally to a coital protective garment useful during sexual activity in preventing skin contact with sexual and body secretions of the other coital partner.

More specifically, the invention relates to a coital protective garment affording barrier protection to the genitals and surrounding skin areas of the lower abdomen and thighs, as a means of precluding skin contact of each of the coital parties with the sexual and body secretions of the other, to assist in the prevention of transmission of sexually transmittable disease.

2. Description of the Related Art

Recent disclosures by the Centers For Disease Control (Washington and Atlanta), and reports at the Third International AIDS Conference in Washington, D.C. in June, 1987, have focused international attention on the proliferation of acquired immune deficiency syndrome (AIDS) in the general population, beyond the orginally defined high risk classification groups of homosexuals, bisexuals, intravenous drug users, and Haitian/African groups.

The diseases with which AIDS has been or is suspected to be linked include Pneumocystis carinii pneumonia, Kaposi's sarcoma, esophageal or bronchopulmonary candidiasis, extrapulmonary cryptococcosis, cytomegalovirus internal organ infection, disseminated Mycobacterium avium complex or M. kansasii infection, chronic herpes simplex ulceration, chronic cryptosporidiosis enteritis, toxoplasmosis of the brain, highgrade B-cell non-Hodgkin's lymphoma, disseminated histoplasmosis, chronic isosporiasis enteritis, and lymphoid interstitial pheumonia in children.

In a recent San Francisco cohort study reported in "AIDS: The Cost in Health and lives," Selik, M. D, Richard M., et al, *The Internist,* April, 1987, pp. 6 et seq, there was found to be, for every case of AIDS in the group studied, nine cases of other HIV-related morbidity. As also reported in this article, cohort follow-up studies indicate that the proportion of HIV-infected persons who will ultimately develop AIDS ranges from 25 percent to 50 percent or more depending on the length of follow-up and the patient's clinical status at the beginning of the study. Mathematical modeling of this trend in reported AIDS cases has led to a projection that the cumulative total of AIDS cases will be 270,000 by 1991, and the number reported that year alone will be 74,000.

Recently reported case studies have included instances where apparent transmission of the AIDS retrovirus (human immunodeficiency virus, or HIV) has been effected by contact of infected blood or saliva with the skin of persons who were later determined to have been infected. One of the reported cases involved the splashing of infected blood from a blood bag onto acned facial skin; another involved apparent transmission via infected saliva contact with a cut on a dentist's finger. These cases suggest that any lacerations, contusions, abrasions, hives, boils, pustules, or other localized discontinuities in the skin surface, may provide a potential entry portal for the retrovirus, resulting in infection by simple skin contact with body fluids, e.g., blood, (including dermal bleeding from injury or disease, and blood from normal menstrual functioning) saliva, semen, etc., from another infected individual.

Inasmuch as a primary mode of infection in the reported cases has been sexual contact with an infected person, the recent findings raise the possibility that contact of skin areas surrounding the genitalia and on the lower torso may, if there are any defects in skin integrity, provide an increased risk of transmission of the virus, even when condoms are employed. Thus, the skin of the groin region, including the lower abdomen and upper thighs may present a possible site for infection during sexual activity, from skin contact with body fluids and sexual secretions of the other coital partner.

In addition to such possible transmission of the AIDS virus by entry through localized skin defects in the recipient, there is also the possibility that other sexually transmitted diseases (STDs) may be similarly transmitted, including clamydia, herpes, papilloma, syphilis, gonorrhea, lymphogranoloma venerum, and the like.

The foregoing has heightened pertinence in view of the fact that localized skin disorders occur with high frequency in the lower abdominal and thigh regions. Examples include infected ingrown pubic hairs, pimples, blackheads, boils, rashes, herpes, dermatitis, allergic reactions, and the like, which, comprise or result in localized skin discontinuities and other defects in skin integrity.

In sum, the potential for dermal invasion of viral and other infectious agents via localized skin defects in the groin area, by contact thereof with sexual and/or other body fluids of an infected person during sexual activity, raises concerns about the reliability of condoms and similar means as effective preventatives for transmission of STDs, particularly in view of the occurrence of groin skin contact with sexual secretions of a coital partner even when condoms are employed.

Accordingly, there is a perceived and perhaps critical need for the provision of means affording enhanced protection to the skin in the groin area, e.g., from the umbilicus to at least the upper thighs, of an individual during sexual activity, which prevent dermal contact with a sexual partner's coital secretions, e.g., semen, seminal fluid, vaginal exudate, etc., in such body region.

There is also a need in the provision of such means to provide protection of a type which does not entail the risk of any secondary infectious contact, such as when a protective or barrier article is removed following intercourse.

It is therefore an object of the present invention to provide such protection means, for avoidance of dermal contact of groin area skin with sexual and body fluids of a coital partner.

It is another object of the invention to provide a protective means of such type, in the form of a protective garment which is readily applied to the person of the wearer, unobtrusively deployed during sexual contact, and subsequently readily removed from the person of the wearer, without the risk of secondary contact with the exterior fluid-contacted surface of the garment article following coitus.

Other objects and advantages will be more fully apparent from the ensuing disclosure and appended claims.

SUMMARY OF THE INVENTION

In one broad aspect, the present invention relates to a coital protective garment, comprising;
 a groin covering panel formed of liquid-impenetrable material; and
 a penile sheath formed of liquid-impenetrable material, leak-tightly joined at its proximal end to the groin covering panel to enable penis insertion into the penile sheath, with the panel being circumferentially continuous around the proximal end of the sheath at its junction with the panel.

In another aspect of the invention broadly described above, the groin covering panel may be the frontal panel portion of a panty-type garment.

In another aspect of the invention broadly described above, the groin covering panel may be provided at its margins with complimentary closure means, such as: skin-adhesive or self-adhesive means, e.g., adhesive appliques, or adhesive coatings; refastenable tapes; hook and loop-type fasteners; or other mechanical fastener means, such as straps equipped at their extremities with Velcro ® fasteners, tongue and buckle elements, or free ends which may be tied to one another about the lower abdominal region of the wearer.

In another aspect of the coital protective garment as broadly described above, the penile sheath is detachably joined to the groin covering panel. The penile sheath may thus constitute a conventional condom, so that the garment, upon replacement or fitting of a condom at the junction with the groin covering panel, may be reused, optionally with disinfection, cleaning or other treatment of the garment subsequent to its initial use.

In another aspect, the coital protective garment of the invention is adapted to be reversibly employed, either in a first mode by being worn by a male person whose penis is inserted into the penile sheath, or in a second mode in which the garment is inverted (turned inside out) with respect to the first mode, whereby the garment may be worn by the recipient coital party, to allow penile insertion by the other partner during intercourse.

In a still further aspect of the invention, there is provided a coital protective garment comprising a groin covering panel formed of liquid-impenetrable material, with a coupling opening in the panel for leak-tight joining of a penile sheath at its proximal end thereto. The panel is circumferentially continuous around the proximal end of the sheath at its junction of the panel, and means are provided for retaining the panel in a coitally accommodating position on the body of a wearer.

Other features and embodiments of the invention will be more fully apparent from the ensuing disclosure and appended claims.

DETAILED DESCRIPTION OF THE INVENTION, AND PREFERRED EMBODIMENTS THEREOF

The coital protective garment of the present invention is intended to provide enhanced protection to the genital, upper thigh, and lower abdominal regions of both coital partners during sexual activity, by preventing contact of the genitals or surrounding skin with the body fluids, particularly sexual secretions, of the other partner. As a result, the risk of transmission of venereal and/or immunosuppressive infections during sexual activity is greatly reduced.

The garment of the invention is suitably formed of low-cost materials of construction so that it is readily and easily disposable following its use. Although some embodiments of the invention are described hereinafter with reference to reuse of the specific garment article, it is highly preferred to employ the coital protective garment as a disposable article, for aesthetic reasons as well as to minimize the risk of transmission of infection which may otherwise be present due to inadequate disinfection or sterilization if the garment is reused.

The garment of the invention is constructed in a particularly preferred embodiment, as more fully described hereinafter, to be reversable in character, so that it may be worn by either a male person whose penis is inserted into the penile sheath of the garment or else in a reversed mode with the article being worn on the person of the recipient coital party, to allow penile insertion into the inverted penile sheath by the other partner during intercourse.

Figure 1:
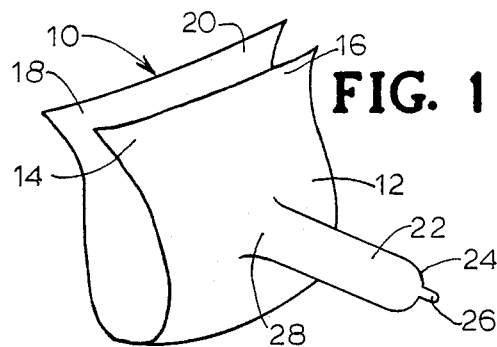
FIG. 1 is a perspective view of a coital protective garment according to one embodiment of the invention, of a wrap-around configuration.

FIG. 1 shows a frontal perspective view of a coital protective garment according to one embodiment of the invention, of a type hereinafter referred to as a "wrap-around" garment.

The illustrated garment 10 comprises a groin covering panel 12 which is formed of a liquid-impenetrable material. Any suitable material may be used for the construction of such panel, provided that it is impenetrable to body fluids, including sexual exudates and secretions. The material should be sufficiently strong so that it does not tear, rip, or otherwise lose its structural integrity under conditions of use, since those conditions will typically involve the application or occurrence of localized stresses, forces, and deformations, incident to penetration and movement involved in the sexual activity. Preferably, the material is highly flexible and resilient in character, e.g., at least partially elastic in character, to maintain such structural integrity under use conditions.

Illustrative of materials which may be potentially useful in the broad practice of the invention are natural and synthetic rubber materials; polymeric materials, including homopolymers and copolymers, e.g., copolymers of the aforementioned rubbers and monomers copolymerizable therewith; and fabrics, such as woven and nonwoven materials, the nonwoven materials including meltblown fiber composites, spunbonded materials, and the like, in which the fabric is either intrinsically liquid impenetrable, or else is treated, or associated with a barrier layer, in a manner imparting such liquid impenetrability characteristics. Laminated materials of various components, such as a multilayer film comprising layers of the same or different composition, may be usefully employed.

A preferred material for the construction of the groin covering panel is latex rubber, due to its ready fabrication, resilient character, formability at low thickness, light weight, and low cost.

Figure 2:
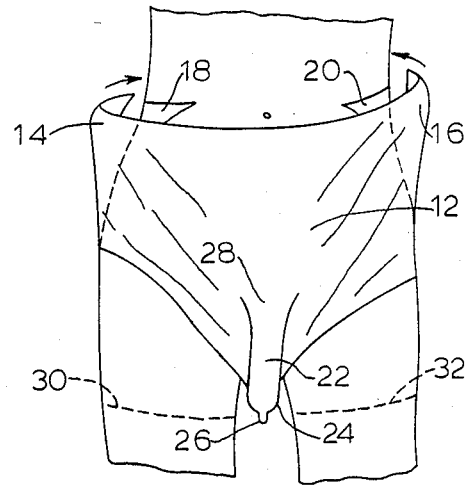
FIG. 2 is a frontal view of the FIG. 1 garment, as applied to the body of a male wearer in a first mode of deployment.

The groin covering panel 12 may, as shown, have a generally rectangular shape. At its margins, in the respective corner sections 14 and 16 of the internal surface of the panel, there may be provided an adhesive or other bonding means or adherent surface area which is configured to retentively mate with the corresponding marginal corner portions 18 and 20 on the body side surface of the panel. Thus, corner 14 is lappingly mated with corresponding corner surface 18 when applied to the wearer's body, as shown in FIG. 2. In like manner, marginal corner surface 16 is lappingly mated with the corner surface 20, as also shown in FIG. 2. In such manner, the garment is secured at the waist of the wearer, with the male wearer's penis inserted into the penile sheath 22 which is integrally formed with the panel.

When the garment shown in FIG. 1 is employed in a reversed mode and worn on the body of the recipient coital party, it is analogously worn, with the marginal corner surfaces 14 and 16 lappingly mated with the corresponding corner surfaces 18 and 20, respectively. In such reversed mode, the penile sheath 22 may be digitally inserted into the recipient coital party's sexual orifice, or the penile sheath may be urged into the recipient sexual orifice incident to penis insertion into such orifice at the commencement of intercourse.

The penile sheath 22 is formed of liquid-impenetrable material, which in the integral construction shown is desirably the same as the material of construction for the groin covering panel, however it is within the purview of the invention to form a garment of the type shown in FIG. 1 wherein the penile sheath portion comprises a different material of construction than the groin covering panel 12.

The garment shown in FIGS. 1 and 2 may be formed in a manner analogous to that employed for formation of conventional condoms of latex rubber or other resilient elastomeric materials, utilizing a male form mandrel on which the latex rubber is deposited. The garment shown in FIG. 1 requires such a mandrel to be placed on a planar forming board whereby the penile sheath and groin covering panel are concurrently integrally formed by deposition of the latex rubber or other material of construction.

Other forming methods may be utilized to construct the coital protective garment shown in FIGS. 1 and 2, including the bonding or other attachment of a separately formed penile sheath element to a groin covering panel featuring a opening about the periphery of which the distal end of the sheath is leak-tightly joined.

Irrespective of whether the integral construction formed in FIG. 1 is unitarily formed, or is constructed from permanently joined constituent groin covering panel and penile sheath elements, the penile sheath will be deployed with the groin covering panel being circumferentially continuous around the proximal end of the sheath at its junction with the panel, to afford the desired skin protection to the pubic, abdominal and leg skin areas, as shown in FIG. 2.

The distal end 24 of the penile sheath may be formed with a tip reservoir 26 as shown, for the collection and retention of ejaculate, in a known manner. Alternatively, the sheath may be formed without such reservoir, and may be otherwise structurally varied by ribbed or surface contoured construction, or in any other manner in which condoms are conventionally constructed.

In the integral construction shown, the proximal end 28 of the penile sheath may be of an increased thickness relative to the other portions of the garment, or may be otherwise reinforced to insure the reliability and structural integrity of the garment in use. Thus, the penile sheath 22 is leaktightly joined at its proximal end 28 to the groin panel 12 to enable penis insertion into the penile sheath, as shown in FIG. 2, or as inverted when the garment is worn by the recipient coital party.

In lieu of the adhesively or mechanically bonded, lappingly mated corner portions of the garment previously described, the respective corners of the groin covering panel may be provided with a coating or impregnated skin-adherent substance, whereby the corners can be adhesively joined to the wearer's skin and subsequent to use readily removed. Alternatively, any suitable fasteners, interlocks, or retention means may be used at the corners or other marginal portions of the garment, to retain same in position in a coitally accommodating position on the body of the wearer.

It will be apparent that the construction of the garment may be varied so that additional protection is provided to the upper thigh regions of the wearer, by appropriate construction so that the leg portions of the wrap-around garment extend to the thigh lines indicated by dotted line representations 30 and 32 in FIG. 2.

The coital protective garment of the invention is desirably constructed and adapted to be reversibly employed in either of dual modes of use. In a first mode, as illustrated with reference to FIG. 2, the garment is worn by a male person whose penis is inserted into the penile sheath. The garment is reversible and may be employed in a second mode, wherein the garment is inverted (turned inside out) relative to the first mode, so that the garment may be worn by the recipient coital party to allow penile insertion by the other partner during intercourse. The inverted penile sheath thus may be inserted by the wearer into the penis-receiving sexual cavity, prior to sexual contact, or the act of penis insertion into the receiving sexual orifice may itself effect the introduction of the penile sheath into such orifice.

Following sexual activity, the corners of the groin covering panel may be disengaged from one another or from adhesive contact with the skin, and the entire garment manually removed from the wearer's body without contact of the exterior surface thereof with the fingers, hands, etc. For example the garment after its use may be "rolled up" with the user's hands contacting only the surface of the garment which has not been contacted with the body fluids of the other coital partner during the use of the garment. In this way, the risk of secondary infectious contact during the removal of the garment is avoided. This feature represents a substantial advantage of the invention relative to the use of condoms, which invariably require contact of the hands with the body fluid-contacted exterior surface of the condom during its removal. A further advantage over condoms is of course the enhanced protection afforded by the invention by virtue of the groin covering panel portion thereof.

Figure 3:
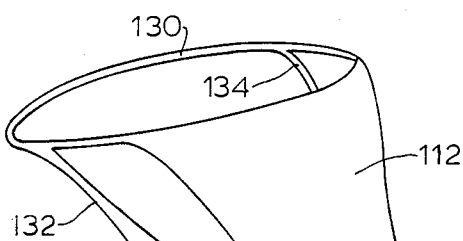
FIG. 3 is a perspective view of a coital protective garment according to another embodiment of the invention.

FIG. 3 is a perspective view of an alternative embodiment according to the invention, having a groin covering panel 112 as the frontal panel portion of the coital protective garment. This garment is formed with a construction analogous to an athletic supporter, but with a penile sheath 122 integrally joined at its proximal portion 128 to the panel, as shown. The penile sheath may be formed in an analogous manner to the sheath of the embodiments shown in FIGS. 1 and 2, with a tip reservoir 126 at its distal end 124.

The groin covering panel 112 may be joined to a waist string element 130 which is elasticized or otherwise resilient in character to compressively retain the garment in place on the body of the wearer. The groin covering panel 112 may also extend rearwardly with a perineal covering portion joined by the retention straps 132 and 134 to the aforementioned waist string 130.

Figure 4:
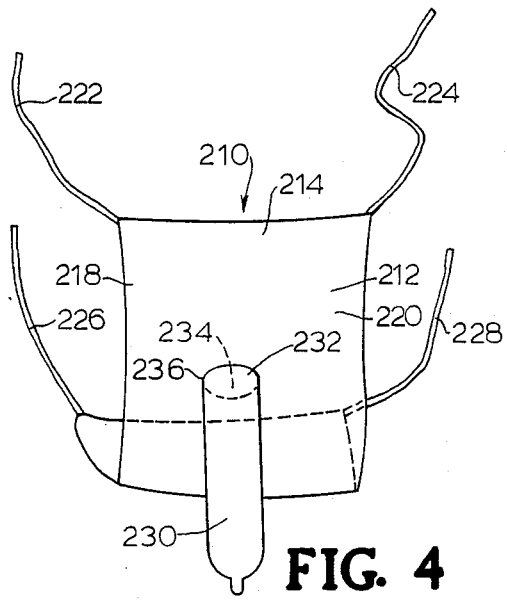
FIG. 4 is a frontal perspective view of a coital protective garment according to yet embodiment of the invention.
Figure 5:
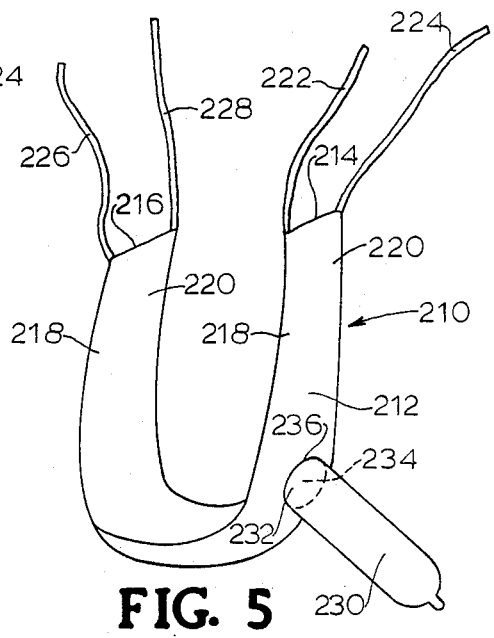
FIG. 5 is a side view of the coital protective garment of FIG. 4, showing the details of construction thereof.

FIGS. 4 and 5 show a coital protective garment according to another embodiment of the invention, of a type hereinafter referred to as an "apron-type" garment.

The illustrated garment 210 comprises a groin covering 212 formed of a liquid-impenetrable material. Referring to FIG. 5, which is a side perspective view of the coital garment of FIG. 4, the groin covering panel 212 is appropriately constructed so that its front upper margin 214 and rear upper margin 216 may be deployed at the waist region of the wearer, with the respective side margins 218 and 220 defining a width of the groin covering panel therebetween which is adequate to provide the desired extent of skin contact protection in the groin region.

Although the groin covering panel is shown as being of rectangular form, it will be appreciated that such panel may be formed with appropriate leg cut-outs in the form of an arcuate contour at an intermediate portion of each side margin, generally equidistant from the upper margins 214 and 216, respectively.

At the corners defined by intersections of the side margins 218 and 220 with the respective upper margins 214 and 216, are provided tie-straps 222 and 224, at the front corners, and tie straps 226 and 228, at the rear corners. These respective tie straps may be correspondingly tied to one another, to serve as means for retaining the groin covering panel in a coitally accommodating position on the body of a wearer.

It will be appreciated that the tie straps shown are illustrative only, and that various other suitable types of securement means could be employed to retain the panel in the desired coitally accommodating position on the wearer's body. For example, in place of the tie straps, there could be provided at the margins of the groin covering panel respective strap elements having tongue and buckle portions at their extremities. Other securement means may include straps having Velcro ®-type fasteners, as hereinafter described in greater detail with reference to the embodiment shown in FIG. 8. Still other potentially useful securement means may include refastenable tapes, or low-tack adhesive appliques or coatings, as provided with a suitable release paper or other removable protective means, in a known manner.

The penile sheath 230, formed of a liquid-impenetrable material, is leak-tightly joined at its proximal end 232 to the groin covering panel 212, to enable penis insertion into penile sheath 230 through the associated penile opening 234 in the groin covering panel. The panel is, as shown, circumferentially continuous around the proximal end of the penile sheath 230 at its junction 236 with the panel.

The coital protective garment illustrated in FIGS. 4 and 5, is of a construction wherein the penile sheath is formed of the same liquid-impenetrable material as the groin covering panel 212, being integrally constructed to form a conjoint structure of the panel and sheath. It is within the purview of the invention, however, to construct the penile sheath of a different liquid-impenetrable material, as compared to the groin covering panel, and to form these elements discretely, or with the groin covering panel constructed as hereinafter described with reference to the embodiments of FIGS. 8 and 9, wherein conventional condoms may be detachably attached to the groin covering panel to form the coital protective garment.

It is also within the purview of the invention to utilize a coital protective garment of the general type shown in FIG. 4 and 5, but utilizing in place of the tie straps shown, webbing or netting members with one such member joining one pair of complimentary side margin portions of the groin covering panel, and the other such member joining the other pair of side margin portions of the groin covering panel, and with such webbing or netting members arranged to provide leg openings in the garment.

As a still further alternative, the frontal portion of the groin covering panel may be provided with snaps, buttons or buttonholes, complimentarily matable to snaps, buttonholes, or buttons on the rear panel portion of the groin covering panel.

Figure 6:
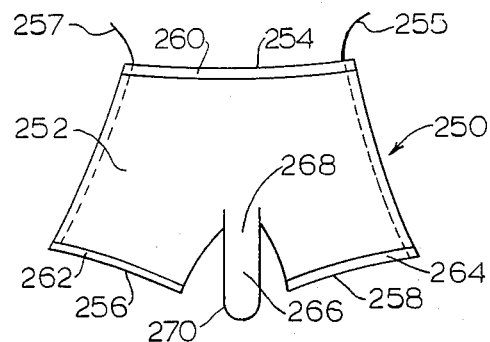
FIG. 6 is a frontal perspective view of a coital protective garment according to another embodiment of the invention, as arranged for wearing by the active sexual partner.
Figure 7:
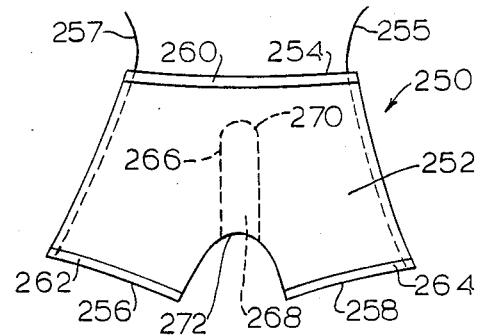
FIG. 7 is a frontal perspective view of the coital protective garment of FIG. 6, inverted (turned inside out) relative to the FIG. 6 orientation, to accommodate wearing by a recipient sexual partner.

Another coital protective garment embodiment of the invention is shown in FIGS. 6 and 7, FIG. 6 showing a front elevation view of a panty-type garment in a first mode of deployment, and FIG. 7 showing a frontal elevation view of the same garment in inverted configuration in a second mode of deployment. The second mode of deployment accommodates insertion of the penis by the other coital partner, with the penile sheath as so inverted being received within the sexual orifice of the recipient coital partner.

The second mode configuration shown in FIG. 7 thus may be obtained from the FIG. 6 configuration by inversion (turning inside out) of the penile sheath, while keeping the same side of the garment outwardly disposed. Alternatively, the main body portion of the garment may itself be inverted, so that the body surface thereof is externally disposed, while keeping the same side of the penile sheath outwardly disposed.

In such manner, the garment construction is of a reversible type, permitting it to be worn by the active male sexual partner in a first mode, or when reversed, in a second mode, by the recipient sexual partner.

With reference to FIGS. 6 and 7, the coital protective garment 250 therein shown is formed with a main body portion 252 defining a brief or panty-type construction, with a waist opening 254 and respective leg openings 256 and 258. Thus, the groin covering panel in the embodiment of FIGS. 6 and 7 is the panel assembly of the body portion 252.

The waist opening 254 of the panty-type garment shown in FIGS. 6 and 7 may be provided with an elasticized waist band 260. In like manner, the respective leg openings 256 and 258 may be provided with elasticized leg bands 262 and 264. Such elasticized waist and leg openings may be provided by sewing strips of thermally heat-shrinkable material around the periphery of these openings, followed by application of heat sufficient to induce shrinkage to the desired degree, or by sewing a gathered elastic material such as materials commercially available under the trademarks Spandex ®, and Lycra ®, or similar materials, around the periphery of these waist and leg openings, or in any other suitable manner known in the art for providing elasticized body part openings in garments.

In lieu of the provision of separate elastic or gathering elements at such opening peripheries, the body portion of the garment may itself be formed of an elastic or elastomeric material which obviates the need for provision of such further retention elements.

In the embodiments shown in FIGS. 6 and 7, the means for retaining the panel and associated penile sheath in a coitally accommodating position on the body of the wearer may be the material itself or its panty-type construction which is continuous around the trunk and perineum of the wearer.

The penile sheath 266 of the garment shown in FIGS. 6 and 7 may be integrally formed with the main body portion 252 of the garment, so as to be continuous at its proximal end 268 with the associated body portion of the garment. Alternatively, the main body portion and penile sheath may be formed as separate elements which are detachably attachable to one another. In such separate element arrangement, the garment may be provided with a suitable opening and retention means for coupling the main body portion of the garment with a condom or other discrete penile sheath element, such as the means illustratively described hereinafter with reference to the embodiments shown in FIGS. 8 and 9.

In the inverted ("second mode") configuration shown in FIG. 7, the penile sheath 266 has been inverted by insertion of its distal end 270 into the interior of the panty-type garment. This provides an external opening 272 for penis insertion by the other coital partner when the garment is worn by the receptive sexual partner, with the inverted penile sheath reposed in or introduced into the sexual orifice of such recipient partner. This inverted configuration is also suitable for sexual interaction without the occurrence of intercourse.

The panty-type coital protective garment shown in FIGS. 6 and 7 may be formed of any suitable material including those illustratively referred to in connection with the wrap-around and apron-type embodiments previously described. The body portion 252 of the garment may be formed of a unitary construction, or as a multipanel assembly, in any suitable manner.

In order to facilitate the ready removal of the garment shown in FIGS. 6 and 7, the garment at its side panel portions may be provided with so-called rip-strings 255 and 257, which when manually grasped at the free end and drawn downwardly will sever the garment at the seamline indicated in dotted line representation on the drawings of FIGS. 6 and 7. In lieu of the construction shown, wherein rip-strings are provided at both side panel portions of the garment, only one such rip-string severing means may be employed.

By so severing the garment, the same may be readily removed from the body of the wearer for subsequent disposal, without contact of the fingers or hands with the exterior surfaces of the garment which have been subjected to contact with body and sexual fluids of the other coital partner during intercourse.

An illustrative method and apparatus of forming panty-type garment articles, which may be adapted to the manufacture of coital protective garments of the present invention, is described in U.S. Pat. No. 4,650,530 to Brian J. Mahoney et al issued Mar. 17, 1987.

Figure 8:
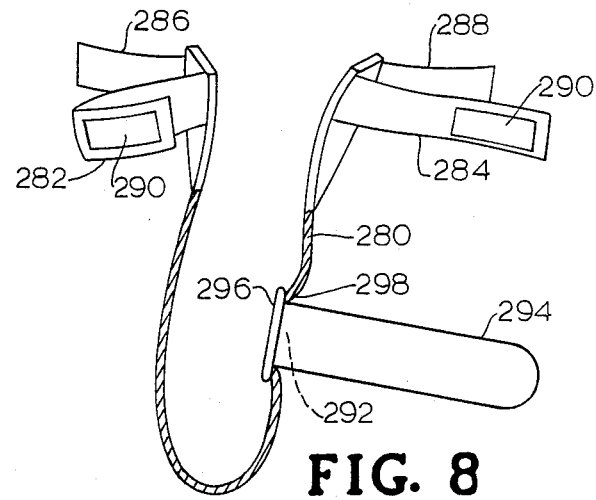
FIG. 8 is a sectional elevational view of a coital protective garment according to another embodiment of the invention, comprising a groin covering panel which is constructed to accommodate successively employed condoms, so that the garment article itself, exclusive of the condom portion thereof, is reusable.

FIG. 8 shows an apron-type coital protective garment according to another embodiment of the invention. In this embodiment, the groin covering panel 280 is provided at its upper side margin portions with respective closure straps 282, 284, 286 and 288. Each of these straps is provided on a matable face thereof with Velcro ® fastener strips 290, by means of which the complimentary matable faces of the strap extremities may be secured to one another around the waist of the wearer.

The groin covering panel 280 in this construction is provided with an opening 292 through which a penile sheath 294 such as a condom may be inserted, with the distal portion 296 of the sheath being compressively retained in position between the pubic bone of the wearer and the inwardly curved lip 298 of the groin covering panel. The lip portion 298 may be suitably reinforced, if necessary or desired, to enhance the leak-tight character of the junction between the sheath 294 and the groin covering panel 280.

By the construction shown in FIG. 8, there is provided a coital protective garment which is readily employed with conventional rolled-type condoms, such that after use, the condom may be discarded and the garment comprising the groin covering panel and securement straps may be cleaned, disinfected, or otherwise treated to render it susceptible of reuse.

It will be appreciated that the apron-type garment shown in FIG. 8 may be readily inverted relative to the configuration shown in the drawing, to accommodate wearing by a recipient coital partner, analogous to the embodiments previously described.

Figure 9:
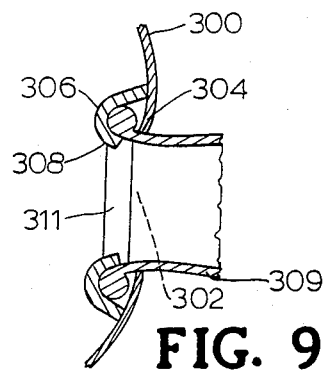
FIG. 9 is a sectional elevation view of a locking means which may be used to secure a condom to the groin covering panel.

FIG. 9 is a sectional elevation view of a portion of a coital protective garment according to the invention, of a type wherein a penile sheath is detachably joined at its proximal end to the groin covering panel, and is fixedly secured in position by structural locking means.

As shown in FIGS. 9, the groin covering panel 300 is provided with an opening 302 which is circumferentially bounded by the inwardly curved lip 304 of the groin covering panel. Circumjacent this lip is an interiorly disposed locking flange 306 whose flange extremity 308 is of a deformable resilient material. The locking flange is biased against the innersurface of the lip 304 when a condom is not mounted in the opening 302.

The penile sheath 309 may be a rolled condom of convential type, having a proximal ring portion 311 when the condom is fully unrolled. The proximal ring is inserted into the circumferential groove defined by the lip 304 and locking flange 306, by manually pressing the ring against the junction of the lip and locking flange extremity, to force these elements apart for introduction of the ring 311 into the resultingly formed groove.

Subsequent to such insertion of the ring into the groove, the resilient flange 306 bears compressively against the ring, so that the penile sheath is compressively held at its proximal extremity between the locking flange 306 and the lip 304. Subsequent to use, the penile sheath may be removed and after any optional cleaning, disinfection, or treatment of the groin covering panel of the garment, the panel may be deployed with a freshly inserted condom.

It is further within the purview of the invention to utilize penile sheath and/or groin covering panels which are coated, impregnated, or otherwise treated with germicides, viricides, contraceptives, lubricants, and/or any other suitable functional materials.

Further, while preferred and illustrative embodiments of the invention have been described, it will be appreciated that numerous modifications, variations, and other embodiments are possible, and accordingly, all such apparent modifications, variations, and embodiments are to be regarded as being within the spirit and scope of the invention.

What is claimed is:

1. A coital protective garment of panty configuration, comprising:
   (a) a main body portion formed of flexible, resilient, liquid-impenetrable material, defining a waist opening and leg openings, and of a size and shape adapted to cover genital, upper thigh, and lower abdominal regions of a wearer, with said material of said main body portion being continuous between the waist opening and each said leg opening at respective sides of the main body portion;
   (b) a non-bellowed, generally smooth-surface tubular penile sheath integrally formed with the main body portion and having a closed distal end, formed of flexible, resilient, liquid-impenetrable material, and integrally leak-tightly joined at its proximal end to the main body portion to enable penis insertion into the penile sheath, with the main body portion being circumscribingly continuous around the flexible end of the sheath at its integral junction with the main body portion; and
   (c) a rip string joined to said main body portion at one of said sides thereof and extending interiorly upwardly therein from a said leg opening over said waist opening to an exterior free end, such that when the free end is manually grasped by a wearer of the garment and drawn downwardly, the rip string will sever the main body portion of the garment at said side thereof between said waist opening and the said leg opening, whereby the garment may be readily removed from the body of the wearer without manual contact by the wearer with exterior surfaces of the garment which have been subjected to contact with body and sexual fluids of an other coital partner when the garment is worn during sexual intercourse.

2. A coital protective garment according to claim 1, comprising rip strings joined to said main body portion, for severing the main body portion of the garment between said waist opening and each said leg opening.

3. A unitary reversible coital protective garment, consisting essentially of:
   a flexible, resilient, liquid-impenetrable panel comprising a planar sheet of substantially rectangular shape having four corners with discrete corner portions at each of said four corners, including a first pair of corner portions at a first end of said sheet and a second pair of corner portions at a second end of said sheet and a mid-section of said panel therebetween, said panel being wrappable about the abdomen of a wearer with the mid-section at the perineum of a wearer and with said first pair of corner portions being laterally lappable with said second pair of corner portions to define a frontal panel section on the frontal abdominal region and a rear panel section on the rear abdominal region when the garment is worn by a wearer, said corner portions being adherent to laterally lapped portions of said sheet upon contact therewith when said panel is wrapped about the abdomen of a wearer with the frontal panel section and the rear panel section being substantially coextensive in size and shape with respect to one another and of sufficient size and shape to cover genital upper thigh, and lower abdominal regions when said panel is wrapped about the abdomen of a wearer;
   a non-bellowed, generally smooth-surfaced tubular penile sheath integrally formed with said sheet and joined at a proximal end of the sheath to said frontal panel section of said sheet, said penile sheath being closed at a distal end thereof and defining at its juncture with the frontal panel section of the sheet an opening in the sheet through which a penis can be inserted into the penile sheath;
   said panel and said sheath being of a same material of construction;
   said garment being continuous over the full structural extend of said panel and said penile sheath;
   said garment being constructed and adapted to be alternatively employable in a selected one of dual modes of deployment comprising (i) a first mode wherein the garment is worn by a male person whose penis is inserted into the penile sheath, and (ii) a second mode therein the garment is worn by a recipient coital party to allow insertion of a penis of an other coital partner into the penile sheath of the garment.

4. A unitary reversible coital protective garment according to claim 3, wherein the liquid impenetrable material of said panel and said sheath portion is selected from the group consisting of rubber materials and polymeric materials.

5. A unitary reversible coital protective garment according to claim 3, wherein said panel and said sheath portion are formed of latex rubber.

6. A unitary reversible coital protective garment according to claim 3, comprising adhesive on at least one of said pairs of corner portions.

* * * * *